United States Patent
Kai et al.

(10) Patent No.: US 6,777,052 B2
(45) Date of Patent: Aug. 17, 2004

(54) PLASTIC CONTAINER CONTAINING ALBUMIN SOLUTION

(75) Inventors: Toshiya Kai, Osaka (JP); Hideaki Murata, Osaka (JP); Makoto Sato, Osaka (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 10/106,185

(22) Filed: Mar. 27, 2002

(65) Prior Publication Data

US 2002/0192411 A1 Dec. 19, 2002

(30) Foreign Application Priority Data

Mar. 27, 2001 (JP) ........................................ 2001-089539

(51) Int. Cl.[7] ........................ B29D 22/00; B29D 23/00; B32B 1/08
(52) U.S. Cl. .................... 428/36.6; 428/36.7; 428/35.7; 428/36.9; 428/36.91; 428/36.92; 206/438; 206/524.1; 422/41; 514/21
(58) Field of Search .............................. 428/34.8, 34.7, 428/35.1, 35.2, 35.4, 35.5, 35.7, 36.6, 36.7, 36.9, 36.91, 36.92; 424/400; 206/438, 524.1; 422/41; 514/21; 530/363; 604/403, 415

(56) References Cited

U.S. PATENT DOCUMENTS

| | | | |
|---|---|---|---|
| 4,630,727 A | 12/1986 | Feriani et al. | ............... 206/221 |
| 4,872,553 A | 10/1989 | Suzuki et al. | ............. 206/524.4 |
| 5,783,382 A | * 7/1998 | Aoyama et al. | ................ 435/4 |
| 6,197,936 B1 | * 3/2001 | Sano et al. | .................. 530/363 |
| 6,326,010 B1 | * 12/2001 | Sano et al. | .................. 424/400 |
| 2002/0124526 A1 | * 9/2002 | Lewis, Jr. et al. | ............ 53/396 |

FOREIGN PATENT DOCUMENTS

| | | |
|---|---|---|
| EP | 1 258 234 A1 | 11/2002 |
| GB | 2 025 895 A | 1/1980 |
| JP | 5-2903159 A | 11/1993 |
| WO | 00/15241 A1 | 3/2000 |

OTHER PUBLICATIONS

"Roche Lexikon Medizin", 1987, Hoffman–La–Roche AG und Urban & Schwarzenberg, München, Wein, Baltimore, XP002251009, pp. 42 and 1363–1365.

Hellerich, Walter, "Werkstoff–Führer Kunststoffe", Kunststoffe, 1996, Carl Hanser Verlag, München, Wein, XP002251010, 1996, pp. 32–33 and 374–377.

* cited by examiner

*Primary Examiner*—Harold Pyon
*Assistant Examiner*—Michael C. Miggins
(74) *Attorney, Agent, or Firm*—Kubovcik & Kubovcik

(57) ABSTRACT

The present invention provides a plastic container containing albumin solution and a packaged plastic container containing an albumin solution. The plastic container containing an albumin solution having an albumin concentration of 1 to 500 mg/ml, has at least one inlet/outlet for a liquid, and has a water vapor permeability of 1.5 g/m²/day·1013.25 hPa or less when the vapor permeability is measured at a pressure of 1013.25 hPa per surface area of 1 m² for 24 hours at a temperature of 25° C. and at a relative humidity of 60%. The plastic container containing an albumin solution can be packaged with an outer packaging material to provide the packaged plastic container.

13 Claims, 1 Drawing Sheet

PLASTIC CONTAINER CONTAINING ALBUMIN SOLUTION

TECHNICAL FIELD

The present invention relates to a plastic container containing an albumin solution. In particular, the present invention relates to a plastic container that allows evaporation of moisture only in an extremely small amount and is capable of storage of the solution for a long period of time.

BACKGROUND ART

Albumin, especially human serum albumin, is a protein which is present in plasma, and which is produced in the liver and has functions of maintaining normal oncotic pressure in blood flow and carrying nutritive substances or metabolites by combining therewith. For this reason, albumin has been considered to be effective in treating injury-related symptoms of patients suffering from hemorrhagic shock, thermal burns and the like and in treating patients suffering from hypoalbuminemia and fetal erythroblastosis. Conventionally albumin has been produced by fractionating blood collected from humans. Further, in recent years, research and development in large-scale production and purification technology of gene recombinant albumin have progressed, and as a result, pharmaceutical preparations for clinical treatment are going to be put on the market. Such albumin is dissolved in purified water to prepare a solution and is administered to a human by injection or clinical infusion.

As a container for receiving an albumin solution, a glass container has heretofore been used. For example, storage in a soft glass container subjected to a dealkalization treatment has been proposed (Japanese Patent Application Laid-open No. Hei 4-210648). Also, it has been proposed to store a human albumin solution in a type II glass vial, for example, silicate glass subjected to a standard surface treatment (treatment with ammonium salt or sulfur oxide, type II glass) (Japanese Patent Application Laid-open No. Hei 9-221431). These glass containers are each intended to avoid release of aluminum therefrom. However, these glass containers have defects in that they are heavy, likely to be destroyed, and the like. Further, a method of injecting these albumin solutions into glass containers has a danger of contamination of the albumin solution in the container with bacteria or other contaminants in the air, and thus such containers are not for general-purpose use.

For use in case of emergency, a lighter container than such glass containers is required. In response to this requirement, use of a plastic container has been studied in recent years. However, the present inventors have found that plastic containers have problems in that albumin is adsorbed on walls of the containers depending on the material thereof, water in the albumin solution evaporates while being stored in the container, and the containers are influenced by gas from the outside coming through the walls of the container such as oxygen, carbon dioxide gas and the like, and are also influenced by light from the outside of the container and so forth. On the other hand, as a pharmaceutical preparation, albumin preparations are required to have little change in quantity of water during storage.

SUMMARY OF INVENTION

The present inventors have made an intensive study in order to solve the above problems. As a result, the present inventors found that by controlling the surface area, wall thickness and plastic material of an albumin container so as to provide a moisture permeability (equivalent to water vapor permeability) and an oxygen permeability within specified ranges at 25° C. and relative humidity of 60%, an albumin container can maintain its performance over a long term, for example, for 800 days or more, thus attaining the present invention.

Therefore, the present invention relates to:

(1) a plastic container containing an albumin solution which has an albumin concentration of 1 to 500 mg/ml, wherein the container has at least one inlet/outlet for liquid, and has a low water vapor permeability of 1.5 g/m$^2$/day·1013.25 hPa or less, when the water vapor permeability is measured at a pressure of 1013.25 hPa per surface area of 1 m$^2$ for 24 hours at 25° C. and at a relative humidity of 60%, (2) a plastic container containing an albumin solution according to the above item 1, wherein the container has a low oxygen permeability of less than 5,000 cm$^3$/m$^2$/day·1013.25 hPa, when the oxygen permeability is measured at a pressure of 1013.25 hPa per surface area of 1 m$^2$ for 24 hours at 25° C. and at a relative humidity of 60%, (3) A plastic container containing an albumin solution according to the above item 1, wherein the container is a single layer or multi layer structure, (4) a plastic container containing an albumin solution according to the above item 1, wherein the container is a single layer structure, (5) a plastic container containing an albumin solution according to the above item 1, wherein the plastic of the plastic container having low water vapor permeability is one or more members selected from the group consisting of polyethylene, polypropylene, polyvinyl chloride, crosslinked ethylene/vinyl acetate copolymer, polyvinylidene chloride, polybutene, polyester and ethylene copolymer, (6) a plastic container containing an albumin solution according to the above item 1, wherein the plastic of the plastic container having low water vapor permeability is polyethylene or polypropylene, (7) a packaged plastic container containing an albumin solution, wherein the plastic container containing an albumin solution of the above item 1 is packaged with an outer packaging, (8) a packaged plastic container containing an albumin solution according to the above item 7, wherein the outer packaging has a low oxygen permeability of less than 5,000 cm$^3$/m$^2$/day·1013.25 hPa, when the oxygen permeability is measured at a pressure of 1013.25 hPa per surface area of 1 m$^2$ for 24 hours at 25° C. and at a relative humidity of 60%, (9) a packaged plastic container containing an albumin solution according to the above item 7, wherein the outer packaging material is one or more members selected from the group consisting of ethylene/vinyl alcohol copolymer, polyvinylidene chloride, polyacrylonitrile, polyvinyl alcohol, polyamide, polyester, acrylonitrile copolymer, polyacrylonitrile, polyethylene terephthalate, polyamide copolymer, polyvinyl chloride, polyester copolymer, and vinylidene chloride copolymer,

(10) a packaged plastic container containing an albumin solution according to the above item 7, wherein the outer packaging material is ethylene-vinyl alcohol copolymer or polyvinyl alcohol,

(11) a packaged plastic container containing an albumin solution according to the above item 7, wherein a disoxidant is placed in the space between the plastic container and the outer packaging,

(12) a packaged plastic container containing an albumin solution according to the above item 7, wherein the plastic container is packaged with the outer packaging under vacuum,

(13) a packaged plastic container containing an albumin solution according to the above item 7, wherein the plastic container is packaged with the outer packaging under nitrogen gas, and

(14) a packaged plastic container containing an albumin solution according to the above item 7, wherein the plastic container is packaged with the outer packaging under light shielding conditions.

Also, the present invention relates to:

(15) a plastic container containing an albumin solution according to the above item 1, wherein the container comprises a multi-layer plastic material having an inner layer, an outer layer and optionally an intermediate layer, at least one of which provides a low water vapor permeability of 1.5 $g/m^2/day \cdot 1013.25$ hPa or less (moisture permeability of $6.25 \times 10^{-3}$ $mg/cm^2/hour$ or less at 25° C. and at humidity of 60%), when the water vapor permeability is measured at a pressure of 1013.25 hPa per surface area of 1 $m^2$ for 24 hours at 25° C. and at a relative humidity of 60%,

(16) a plastic container containing an albumin solution according to the above item 15, wherein the plastic container comprises a multi-layer plastic material having an inner layer, an outer layer and optionally an intermediate layer, at least one of which is a plastic layer providing low oxygen permeability,

(17) a plastic container containing an albumin solution according to the above item 15, wherein the plastic container comprises a multi-layer plastic material having an inner layer, an outer layer and optionally an intermediate layer, at least one of which provides a low oxygen permeability of less than 5,000 $cm^3/m^2/day \cdot 1013.25$ hPa, when the oxygen permeability is measured at a pressure of 1013.25 hPa per surface area of 1 $m^2$ for 24 hours at 25° C. and at a relative humidity of 60%,

(18) a plastic container containing an albumin solution according to the above item 16, wherein the plastic providing low oxygen permeability is one or more members selected from the group consisting of ethylene/vinyl alcohol copolymer, polyvinylidene chloride, polyvinyl chloride, polyvinyl alcohol, polyamide, polyamide copolymer, polyester, polyester copolymer, polyacrylonitrile, acrylonitrile copolymer, polystyrene, polyethylene, polypropylene and vinylidene chloride copolymer, and

(19) a plastic container containing an albumin solution according to the above item 16, wherein the container is molded from a mixture of materials selected from the following low water vapor permeability material group and low oxygen permeability material group.

TABLE 1

| Low water vapor permeability material group | Low oxygen permeability material group |
| --- | --- |
| polyethylene, polypropylene, polyvinyl chloride, crosslinked ethylene/vinyl acetate copolymer, polybutene, polyester, ethylene copolymer, polyvinylidene chloride | ethylene/vinyl alcohol copolymer, polyvinylidene chloride, polyacrylonitrile, polyvinyl alcohol, polyamide, polyester, acrylonitrile copolymer, polyamide copolymer, polyvinyl chloride, polyester copolymer, vinylidene chloride copolymer |

The albumin solution of the present invention is a solution of an albumin concentration of 1 to 500 mg/ml obtained by dissolving serum albumin of a molecular weight of about 67,000 in, for example, water for injection. The serum albumin includes serum albumin purified from human serum or recombinant human serum albumin produced by a genetic engineering technique and so forth. The serum albumin purified from human serum includes, for example, human serum albumin obtained by fractionating blood collected from a human and purifying the obtained aqueous solution containing serum albumin by use of various purifying means. Further, the recombinant human serum albumin produced by a genetic engineering technique includes recombinant human serum albumin obtained by isolating a gene encoding human serum albumin, incorporating it into a suitable vector, introducing the obtained recombinant vector into a suitable host to obtain a transformant, cultivating the transformant, and purifying a culture extract after the cultivation by use of various purification techniques. The purifying means includes, for example, a method combining an ethanol fractionation, PEG fractionation, ammonium sulfate fractionation, an anion exchanger and heat treatment at 60° C. for 10 hours (Japanese Patent Application Laid-open No. Hei 2-191226), methods combining anion exchanger treatment, cation exchanger treatment and heat treatment at 60° C. for 10 hours (Japanese Patent Applications Laid-open Nos. Hei 3-17123 and Hei 7-330626) and so forth.

Preferably, the albumin solution of the present invention contains a stabilizer such as an acetyltryptophan salt, an organic carboxylic acid having 6 to 18 carbon atoms or a salt thereof. For such a stabilizer, for example, acetyltryptophan, it is preferable that about 20 to 60 mg thereof is contained per 1 g of albumin contained in the albumin solution. Examples of the organic carboxylic acid having 6 to 18 carbon atoms include caproic acid, caprylic acid, capric acid, lauric acid, palmitic acid, oleic acid and so forth. Examples of salts of the organic carboxylic acid include salts of alkali metal such as sodium and potassium, and salts of alkali-earth metals such as calcium.

The container for containing an albumin solution of the present invention has at least one inlet/outlet for liquid. Its shape is optional and is, for example, one as shown in FIG. 1. The inlet/outlet for liquid is made of a material that is preferably a hard plastic, for example, polypropylene or polyethylene.

The shape of the container (having at least one inlet/outlet for liquid) is not particularly limited but it is preferable that its capacity for an aqueous albumin solution is usually 10 to 2,000 ml and that it has such a space in its inside that dischargeability of the liquid from the container is good.

The thickness of the walls of the plastic container is desirably in the range of usually 10 to 1,000 μm and, preferably, 50 to 500 μm, so that it is possible to visually check for insoluble matter and the like in the solution contained therein and the dischargeability of albumin solution is good. Most preferably, the thickness of the walls of the plastic container is in the range of 100 to 400 μm. In the case where the surface area of the plastic container is smaller than 100 cm$^2$, the thickness of the walls of the plastic container is preferably in the range of 200 to 400 μm. The water vapor permeability and oxygen permeability of the container depend on the material of the plastic container and/or the thickness of the walls of the plastic container.

The water vapor permeability and oxygen permeability also vary depending on the surface area of the plastic container, even if the kinds of material of plastic container and the thickness of the walls of the plastic container are identical. It is necessary to increase the thickness of the walls of the plastic container in case of the small surface area, since the water vapor permeability and oxygen permeability are required to be low for maintaining the stability of albumin. A thickness of the walls of the container of less than 10 μm is not preferable since water evaporation increases with a simultaneous increase in oxygen permeability and, besides, the strength of the container decreases. A thickness of walls of the container exceeding 1,000 μm results a in decrease in the dischargeability of the aqueous albumin solution during use and at the same time transparency of the container decreases. Thus, it is difficult to observe insoluble foreign matter and denatured albumin in the solution.

The above-mentioned plastic container may be either a single layer structure or of a multilayer structure. A single layer structure is preferred.

Since the albumin solution is a protein preparation, it is susceptible to influences of heat, chemicals and so forth. Therefore, it is preferable to avoid reaching a high temperature when it is filled and it is also preferable that the material that directly contacts the solution is made of polypropylene, polyethylene or the like. Further, in order to ensure the necessary limitation regarding water vapor permeability or oxygen permeability, the container may be a multilayer structure having an intermediate layer and an outer layer.

The method for producing such a plastic container includes a blow molding method and an inflation method (injection molding method). To produce the plastic container of the present invention, either one of these production methods may be used.

The container for containing an albumin solution of the present invention is characterized by having a water vapor permeability of 1.5 g/m$^2$/day·1013.25 hPa or less (i.e., 6.25×10$^{-3}$ mg/cm$^2$/hour·1013.25 hPa or less), when the water vapor permeability is measured at a pressure of 1013.25 hPa per surface area of 1 m$^2$ for 24 hours at a temperature of 25° C. and at a relative humidity of 60%. In the case where the container shows a water vapor permeability above this value, the concentration of albumin in the albumin solution becomes an excessive concentration of 110% or more of the indicated amount, when stored for a long period of time, for example, for 800 days or more, and thus such a container is not preferable. The measurement of the water vapor permeability is performed in accordance with a gravimetric method.

The plastic container whose water vapor permeability described above is within the above-mentioned range may be of a single layer structure or of a multilayer structure, but at least one layer of those provides a water vapor permeability of 1.5 g/m$^2$/day·1013.25 hPa or less (i.e., 6.25×10$^{-3}$ mg/cm$^2$/hour·1013.25 hPa or less) when the water vapor permeability is measured at a pressure of 1013.25 hPa per surface area of 1 m$^2$ for 24 hours at 25°C. and at relative humidity of 60%.

The material that brings about the above-mentioned properties can be selected from polyolefin based resins, chlorine based resins, polyamide based resins, polyester based resins, polyacrylonitrile based resins or a copolymer thereof. Specific examples thereof include ethylene/vinyl alcohol copolymer, polyvinylidene chloride, polyvinyl chloride, polyvinyl alcohol, polyamide, polyamide copolymer, polyester, polyester copolymer, polyacrylonitrile, acrylonitrile copolymer, polystyrene, vinylidene chloride copolymer, polyethylene, polypropylene, polyvinyl chloride, crosslinked ethylene/vinyl acetate copolymer, polyvinylidene chloride, polybutene, and ethylene copolymer. Polyethylene, polypropylene, crosslinked ethylene/vinyl acetate copolymer, polyvinylidene chloride, polybutene, polyester and ethylene copolymer are preferred. These resins may be used singly or in admixture.

Examples of polyamide copolymer include capramide/hexamethyleneadipamide copolymer, capramide/hexamethylenesebacamide copolymer and hexamethyleneadipamide/hexamethylenesebacamide copolymer. Examples of polyester copolymer include aromatic ester-aliphatic ester copolymer and aromatic ester/aromatic ester copolymer. Examples of acrylonitrile copolymer include acrylonitrile/styrene copolymer, acrylonitrile/isobutylene copolymer, acrylonitrile/butadiene copolymer and acrylonitrile/vinyl acetate copolymer. Examples of ethylene copolymer include ethylene/vinyl acetate copolymer, ethylene/vinyl alcohol copolymer, ethylene/1-butene copolymer and ethylene/vinyl chloride copolymer.

It is preferred that the plastic container has the above-described water vapor permeability and, at the same time, an oxygen permeability at a specified value or smaller. Further, it is preferred that albumin is difficult to be adsorbed thereon.

The oxygen permeability is preferably less than 5,000 cm$^3$/m$^2$/day·1013.25 hPa when the oxygen permeability is measured at a pressure of 1013.25 hPa per surface area of 1 m$^2$ for 24 hours at a temperature of 25° C. and at a humidity of 60%. Examples of materials providing the above-mentioned water vapor permeability and, at the same time, the above-mentioned oxygen permeability include ethylene/vinyl alcohol copolymer, polyvinylidene chloride, polyvinyl chloride, polyvinyl alcohol, polyamide, polyamide copolymer, polyester, polyester copolymer, polyacrylonitrile, acrylonitrile copolymer, polystyrene, polyethylene, polypropylene, vinylidene chloride copolymer and so forth among the above-mentioned resins.

The plastic container may be either a single layer structure or a multilayer structure but the layer that contacts the albumin solution is preferably made of a material that is difficult to adsorb albumin.

The plastic having small absorbability of the above-mentioned albumin is selected from polyolefin based resins, chlorine based resins, polyamide based resins, polyester based resins, polyacrylic resins and a copolymer thereof among the above-mentioned plastics having a water vapor permeability and an oxygen permeability as mentioned above. In particular, examples include ethylene/vinyl alcohol copolymer, polyvinylidene chloride, polyvinyl chloride, polyvinyl alcohol, polyamide, polyamide copolymer, polyester, polyester copolymer, polyacrylonitrile, acrylonitrile copolymer, polyethylene, polypropylene, crosslinked ethylene/vinyl acetate copolymer, polybutene, and butene/ethylene copolymer. The absorbability of albumin can be judged by an immersion method.

In the case where the plastic container comprises a single layer structure, preferably it is made of a mixture of at least one, preferably two or three or more, resin(s) each selected from two groups; i.e., one group consisting of polyethylene, polypropylene, polyvinyl chloride, crosslinked ethylene/vinyl acetate copolymer, polyvinylidene chloride, polybutene, polyester, and ethylene copolymer, which are plastics having small water vapor permeability, and another group consisting of ethylene/vinyl alcohol copolymer, polyvinylidene chloride, polyvinyl chloride, polyvinyl alcohol, polyamide, polyamide copolymer, polyester, polyester copolymer, polyacrylonitrile, acrylonitrile copolymer polystyrene, and vinylidene chloride copolymer, which are plastics having small oxygen permeability. Among others, polyethylene and polypropylene are preferred.

The multi-layer plastic container having a plurality of layers (an inner layer and an outer layer and, optionally, an intermediate layer as needed) is a plastic container in which at least one layer provides a water vapor permeability of 1.5 g/m²/day·1013.25 hPa or less (i.e., $6.25 \times 10^{-3}$ mg/cm²/hour or less), when the water vapor permeability is measured at a pressure of 1013.25 hPa per surface area of 1 m² for 24 hours at 25° C. and at relative humidity of 60%.

The thickness of the inner layer, intermediate layer and outer layer may be selected arbitrarily, but at least one layer thereof must satisfy the water vapor permeability and oxygen permeability limitation of the present invention. Further, for performing heat sealing when seal molding a container, it is desirable that the innermost layer is made of a material that has the above-mentioned water vapor permeability and oxygen permeability and can be heat-sealed at relatively low temperatures.

After pouring an albumin solution into the container, the container may be sterilized with steam or hot water. In such a case, the temperature is required to be a temperature (70° C. or less) that does not cause denaturation of albumin.

The plastic container containing an aqueous albumin solution of the present invention may be provided with an outer packaging having a small oxygen permeability (having an oxygen permeability of less than 5,000 cm³/m²/day·1013.25 hPa when the oxygen permeability is measured at a pressure of 1013.25 hPa per surface area of 1 m² for 24 hours at a temperature of 25° C. and at a relative humidity of 60%). The shape of the outer packaging is not particularly limited but desirably it is a thin film in consideration of handling under normal conditions. The thickness thereof is usually 5 to 1,000 μm, preferably 10 to 500 μm.

In this instance, to further suppress the influence of oxygen, the space between the container containing an aqueous albumin solution and the outer packaging material may be exchanged with an inert gas, for example, nitrogen, or filled with an oxygen absorbent (disoxidant).

Further, to further suppress the influence of oxygen, the space above the albumin solution in the plastic container containing an aqueous albumin solution may be rendered under a vacuum or exchanged with an inert gas, for example, nitrogen.

The outer packaging providing a small oxygen permeability may be of the same material as the body of the container or different therefrom.

The method of injecting an albumin solution into the above-mentioned container includes a method of aseptically filling simultaneously with blow molding of the container, a method of filling in a previously molded container and so forth. Any filling method can be used as long as the quality of the albumin solution is not affected.

The container filled with an aqueous albumin solution of the present invention must be heat-sterilized as needed to inactivate virus and the like that may contaminate the albumin preparation. Desirably, heating is carried out under sterilization conditions at 40 to 60° C. for 0.5 to 20 hours.

The containers containing an albumin solution are desirably preserved at 5° C. to 50° C. and at a relative humidity of 10% or more in order to avoid freezing and denaturation.

BEST MODES FOR CARRYING OUT THE INVENTION

The present invention will be illustrated in detail by way of examples hereinafter.

In the examples, measurements of water vapor permeability, oxygen permeability, albumin absorbability, and quantitative analysis of albumin were performed in accordance with the following methods.

Water vapor permeability (or water evaporation amount) calculated from a change in weight of a container filled with an albumin solution during storage (gravimetric method). Oxygen permeability: measured by a differential pressure method. Albumin absorbability: measured by an immersion method. Quantitative analysis of albumin: measured by the BCG method.

In the examples, humidity means relative humidity, and relative humidity is sometimes abbreviated as RH, % means weight/volume %, and human serum albumin is abbreviated as albumin or HSA, unless otherwise specified.

EXAMPLE 1

Figure 1:
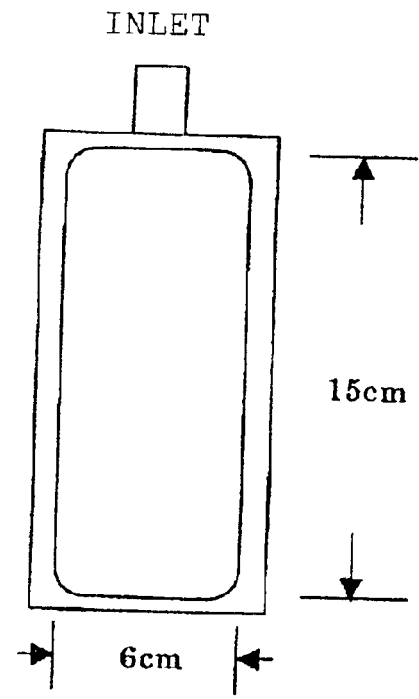
FIG. 1 shows a plan view showing a plastic container prepared in Example 1 of the present invention.

A plastic container having a thickness of 250 μm and a surface area of 180 cm² and having a shape as shown in FIG. 1 (having at least one inlet/outlet for a liquid) was produced by an extrusion molding method with linear low density polyethylene (density: 0.919 g/cm³, oxygen permeability:

7,560 cm ($25^3$ μm)/m²·24 hr·1013.25 hPa at 23° C. and 50% RH, produced by Idemitsu Petrochemical Co., Japan) by use of a general purpose extruder. An inlet/outlet for a liquid made of polypropylene was attached by heat bonding.

50 ml of an aqueous 25% albumin solution was filled in the container and the inlet/outlet was tightly sealed with a plastic plug. The sealed container was stored under conditions of a temperature of 25° C. and humidity of 60% for 6 months and then water evaporation amount was measured from a change in weight of the container with a lapse of time. As a result, the water evaporation amount from the container was 0.25 g/m²/day·1013.25 hPa. At this rate, about 3.3 g of water will evaporate during two years' storage.

EXAMPLE 2

A container was produced having a thickness of 150 μm and a surface area of 180 cm² and having the same shape as that of the container of Example 1 with polypropylene (propylene/α-olefin copolymer (Mitsubishi SPX8600LD), produced by Mitsubishi Chemical Co., Japan). In this container, exactly 50 mL of an aqueous 25% human serum albumin solution was filled and the container was sealed. This container was stored under conditions of a temperature of 25° C. and humidity of 60% for 6 months and then water evaporation amount was measured from a change in weight of the body of the container with a lapse of time. As a result, the water evaporation amount from the container was 0.22 g/m²/day·1013.25 hPa.

EXAMPLE 3

A multilayer film having three layers consisting of a 100 μm layer of linear low density polyethylene (density: 0.919 g/cm³, produced by Idemitsu Petrochemical Co.) as an inner layer, a 50 μm ethylene/vinyl alcohol copolymer (EVAL EF-F, produced by Kuraray Co.) layer as an intermediate layer, and, as the outer layer, a 100 μm layer of the same polyethylene as the inner layer was produced by an extrusion molding method. A container having a surface area of 180 cm² which has the same shape as that of the container of Example 1 was produced therewith. In this container, exactly 50 ml of an aqueous 25% human serum albumin solution was filled and the container was sealed. This was stored under conditions of a temperature of 25° C. and humidity of 60% for 6 months and then a water evaporation amount was measured from a change in weight of the body of the container with a lapse of time. As a result, the water evaporation amount from the container was 0.23 g/m²/day·1013.25 hPa.

The oxygen permeability was 0.5 cm³/m²·24 hr·1013.25 hPa.

EXAMPLE 4

The plastic container containing an aqueous albumin solution (filled with 50 ml of aqueous 25% albumin solution) as produced in Example 1 was stored under conditions of a temperature of 40° C. and humidity of 75% for 3 months in a form of being (1) packaged with nitrogen gas exchange, (2) packaged with a disoxidant, (3) filled with nitrogen gas exchange and packaged with a disoxidant, (4) with outer packaging only, or (5) without any outer packaging, by use of the following 4-layer outer packaging material (produced by Fujimori Kogyo, Japan) having low oxygen permeability (oxygen permeability of 0.5 cm³/m²·24 hr·1013.25 hPa at 25° C. and at 60% RH) The disoxidant was placed in the space between the inner container and the outer packaging material. Further, the plastic container containing an aqueous albumin solution as produced in Example 3 (filled with 50 ml of aqueous 25% albumin solution) was stored under the same storage conditions as above without any outer packaging for 3 months. As a control, a commercially available glass vial preparation (25% BUMINATE, produced by Baxter Co., U.S.A.) was stored under the same conditions as described above. Outer packaging material:

| First layer (innermost layer) | Polyethylene | 40 μm |
|---|---|---|
| Second layer | Silica-deposited polyethylene terephthalate | 12 μm |
| Third layer | Polyethylene terephthalate | 12 μm |
| Fourth layer (outermost layer) | Polyethylene | 60 μm. |

Evaluation of the container was practiced on the albumin solution taken out from the container by quantitative analysis of albumin therein, a change in absorption spectrum thereof (350 to 700 nm), observation of color tone thereof and foreign matter therein by the naked eye. The results are shown in Table 2.

TABLE 2

| Sample | Albumin Content | Absorption Spectrum | Color Tone (Naked Eye) | Foreign Matter (Naked Eye) |
|---|---|---|---|---|
| (1) | 100.5 | No change | No change | None |
| (2) | 100.1 | No change | No change | None |
| (3) | 100.6 | No change | No change | None |
| (4) | 99.6 | Almost no change | No change | None |
| (5) | 100.0 | Changed | Deep brown | None |
| Example 3 | 100.2 | No change | No change | None |
| Control (commercial product) | 99.9 | — | — | None |

In the above-mentioned absorption spectra, no change indicates that the degree of shift or loss of absorption optimum wavelength near 404 nm is of the same level as that of the commercial product and in the case where any change was perceived, such was indicated as changed.

In the above-mentioned color tone, no change indicates that the color tone is the same as that of the control.

As is apparent from Table 2 above, in samples (1) to (4) no change was determined in the content of albumin received and no generation of foreign matter was observed. In the case of storage without any outer packaging, a change in absorption spectrum and coloring were observed (Sample (5)). On the other hand, with respect to coloring, substantially the same level of stability as that of a commercially available vial preparation could be obtained (sample (4)) by provision of an outer packaging material having low oxygen permeability. However, further stabilized preparations could be obtained (samples (1) to (3)) by being packaged with a disoxidant or exchanged with nitrogen exchange.

In the case of the container produced in Example 3, it showed the same level of stability as that of the vial preparation as a control in all the items without being provided with an outer packaging.

TEST EXAMPLE 1

25% HSA (trade name: BUMINATE, produced by Baxter Co. U.S.A.) was aseptically diluted 5-fold with water for injection and 3 ml aliquots thereof were dispensed into 5 ml vials that had been sterilized. Two 0.8 cm in length×2.5 cm in width sheets each of polypropylene (PP), polyethylene (PE), polyvinyl chloride (PVC), and ethylene/vinyl alcohol copolymer (EVOH), sterilized with alcohol, were dipped in the albumin solution of the vials and were sealed. Each sheet was taken out after 1, 3 or 9 days and the concentration of albumin in the solution was measured. For the assay of albumin, a conventional method (BCG method) was used. The results are shown in Table 3.

The water vapor permeability and oxygen permeability of these materials are as follows.

|  | Water vapor permeability (g/m$^2$/day · 1013.25 hPa) | Oxygen permeability (cm$^3$/m$^2$/day· 1013.25 hPa) |
| --- | --- | --- |
| PP | 0.22 (150 μm) | 550 (150 μm) |
| PE | 0.25 (250 μm) | 800 (250 μm) |
| PVC | 0.8 (250 μm) | 65 (250 μm) |
| EVOH | 1.1 (250 μm) | 0.04 (250 μm) |

TABLE 3

| Number of Days Elapsed | PP | PE | PVC | EVOH |
| --- | --- | --- | --- | --- |
| 1 | 99.6 ± 1.6 | 99.9 ± 2.1 | 100.1 ± 1.4 | 99.4 ± 1.8 |
| 2 | 100.0 ± 1.2 | 100.2 ± 1.0 | 100.1 ± 2.0 | 99.4 ± 1.9 |
| 3 | 100.1 ± 0.4 | 101.3 ± 1.1 | 100.9 ± 1.8 | 100.4 ± 0.3 |

The above-mentioned materials which are generally used as a plastic container for medical preparations for injection showed an albumin residue of almost 100% and showed no adsorption, so that they can be used for an albumin solution-receiving plastic container.

COMPARATIVE EXAMPLE 1

Figure 2:
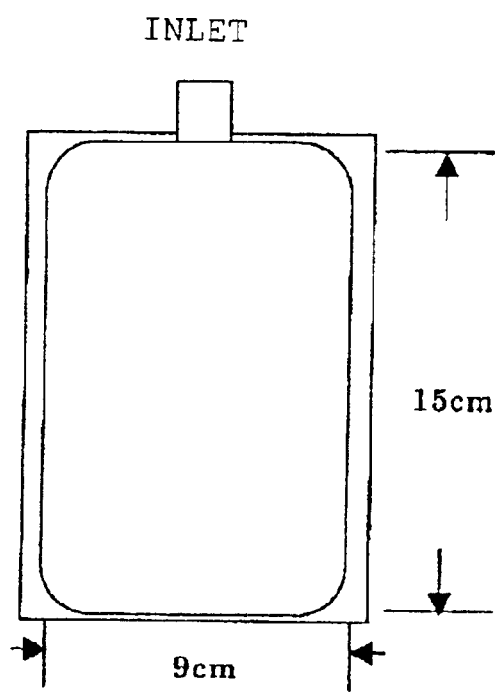
FIG. 2 shows a plan view of a plastic container prepared in the Comparative Example.

A plastic container having a thickness of 50 μm and a surface area of 1,600 cm$^2$ and having a shape as shown in FIG. 2 was produced with linear low density polyethylene (density: 0.919 g/cm$^3$, oxygen permeability: 7,560 cm$^3$ (25 μm)/m$^2$·24 hr·1013.25 hPa at 23° C. and 50% RH, produced by Idemitsu Petrochemical Co.). In this container, exactly 1,000 ml of an aqueous 5% human serum albumin solution was filled and the container was sealed. This was stored under conditions of a temperature of 25° C. and humidity of 60% for 6 months and then water permeability was measured from a change in weight of the body of the container with a lapse of time. As a result, the obtained water evaporation amount was 1.67 g/m$^2$/day·1013.25 hPa. It is presumed that the water evaporation amount when storing this preparation for 2 years will be on the order of 195 g, which means that the albumin concentration will increase to about 6.2 w/v %, so that a change in osmotic pressure, occurrence of insoluble foreign matter and so forth by concentrating by 10% or more are anticipated.

Also, comparing the preparation with the preparation of Example 1, the coloring during the storage is considerable and foaming is vigorous during carrying and occurrence of foreign matter was observed.

INDUSTRIAL APPLICABILITY

A plastic container containing an albumin solution of the present invention allows an extremely small amount of water evaporation from the albumin solution and enables a long-term storage of the solution. During storage, appearance of the albumin solution does not change and the reduction of albumin is extremely small.

What is claimed is:

1. A plastic container containing an albumin solution having an albumin concentration of 1 to 500 mg/ml, the container having at least one inlet/outlet for liquid, and a water vapor permeability of 1.5 g/m$^2$/day·1013.25 hPa or less, when the water vapor permeability is measured at a pressure of 1013.25 hPa per surface area of 1 m$^2$ for 24 hours at 25° C. and at a relative humidity of 60% wherein the wall thickness of the plastic conainer is from about 100 to about 400 μm, and wherein the surface area is from about 22 to about 768 cm$^2$.

2. A plastic container containing an albumin solution according to claim 1, wherein the container has an oxygen permeability of less than 5,000 cm$^3$/m$^2$/day·1013.25 hPa, when the oxygen permeability is measured at a pressure of 1013.25 hPa per surface area of 1 m$^2$ for 24 hours at 25° C. and at a relative humidity of 60%.

3. A plastic container containing an albumin solution according to claim 1, wherein the container is a single layer or multi layer structure.

4. A plastic container containing an albumin solution according to claim 1, wherein the container is a single layer structure.

5. A plastic container containing an albumin solution according to claim 1, wherein the plastic comprises one or more members selected from the group consisting of polyethylene, polypropylene, polyvinyl chloride, crosslinked ethylene/vinyl acetate copolymer, polyvinylidene chloride, polybutene, polyester and ethylene copolymer.

6. A plastic container containing an albumin solution according to claim 1, wherein the plastic is polyethylene or polypropylene.

7. A packaged plastic container containing an albumin solution, comprising the plastic container containing an albumin solution as claimed in claim 1 provided in an outer packaging.

8. A packaged plastic container containing an albumin solution according to claim 7, wherein the material of the outer packaging has an oxygen permeability of less than 5,000 cm$^3$/m$^2$/day·1013.25 hPa, when the oxygen permeability is measured at a pressure of 1013.25 hPa per surface area of 1 m$^2$ for 24 hours at 25° C. and at a relative humidity of 60%.

9. A packaged plastic container containing an albumin solution according to claim 7, wherein the material of the outer packaging comprises one or more members selected from the group consisting of ethylene/vinyl alcohol copolymer, polyvinylidene chloride, polyacrylonitrile, polyvinyl alcohol, polyamide, polyester, acrylonitrile copolymer, polyacrylonitrile, polyethylene terephthalate, polyamide copolymer, polyvinyl chloride, polyester copolymer, and vinylidene chloride copolymer.

10. A packaged plastic container containing an albumin solution according to claim 7, wherein the material of the outer packaging is ethylene/vinyl alcohol copolymer or polyvinyl alcohol.

11. A packaged plastic container containing an albumin solution according to claim 7, wherein a disoxidant is provided between the plastic container and the outer packaging.

12. A packaged plastic container containing an albumin solution according to claim 7, wherein the plastic container is packaged with the outer packaging under vacuum.

13. A packaged plastic container containing an albumin solution according to claim 7, wherein the plastic container is packaged with the outer packaging under nitrogen gas.

* * * * *